US008828054B2

(12) United States Patent
Caborn et al.

(10) Patent No.: US 8,828,054 B2
(45) Date of Patent: Sep. 9, 2014

(54) METHOD AND APPARATUS FOR MENISCAL REPAIR

(75) Inventors: David Caborn, Goshen, KY (US);
Dennis McDevitt, Raleigh, NC (US);
Akbar Nawab, Louisville, KY (US);
Vincent Novak, Longmont, CO (US)

(73) Assignee: Liavatec Corporation, Largo, FL (US)

( * ) Notice: Subject to any disclaimer, the term of this patent is extended or adjusted under 35 U.S.C. 154(b) by 26 days.

(21) Appl. No.: 12/782,600

(22) Filed: May 18, 2010

(65) Prior Publication Data

US 2011/0071549 A1    Mar. 24, 2011

Related U.S. Application Data

(63) Continuation-in-part of application No. 12/417,571, filed on Apr. 2, 2009.

(60) Provisional application No. 61/072,683, filed on Apr. 2, 2008, provisional application No. 61/135,149, filed on Jul. 17, 2008, provisional application No. 61/208,294, filed on Feb. 23, 2009.

(51) Int. Cl.
*A61B 17/04*    (2006.01)

(52) U.S. Cl.
CPC ..... *A61B 17/0401* (2013.01); *A61B 2017/0409* (2013.01); *A61B 2017/0496* (2013.01); *A61B 2017/0456* (2013.01); *A61B 2017/0417* (2013.01); *A61B 17/0466* (2013.01)
USPC .......................................................... 606/232

(58) Field of Classification Search
USPC .......................... 606/139, 228, 232, 144, 151
See application file for complete search history.

(56) References Cited

U.S. PATENT DOCUMENTS

| 3,209,422 A | 10/1965 | Dritz |
| 3,399,432 A | 9/1968 | Merser |
| 3,527,223 A | 9/1970 | Shein |
| 3,716,058 A | 2/1973 | Tanner, Jr. |
| 3,931,667 A | 1/1976 | Merser et al. |
| 3,990,619 A | 11/1976 | Russell |
| 4,006,747 A | 2/1977 | Kronenthal et al. |
| 4,235,238 A | 11/1980 | Ogiu et al. |
| 4,586,502 A | 5/1986 | Bedi et al. |
| 4,635,637 A | 1/1987 | Schreiber |
| 4,649,952 A | 3/1987 | Jobe |
| 4,669,473 A | 6/1987 | Richards et al. |
| 4,736,746 A | 4/1988 | Anderson |
| 4,741,330 A | 5/1988 | Hayhurst |
| 4,823,794 A | 4/1989 | Pierce |

(Continued)

FOREIGN PATENT DOCUMENTS

| WO | WO 01/39671 | 6/2001 |
| WO | WO 02/36020 | 5/2002 |

(Continued)

*Primary Examiner* — Katherine M Shi
(74) *Attorney, Agent, or Firm* — Pandiscio & Pandiscio

(57) ABSTRACT

A method for securing a first object to a second object, the method comprising providing a suture and a plurality of cleats slidably mounted on the suture; passing one end of the suture and a first cleat through the first object and the second object; tensioning the suture so as to secure the suture to the first cleat; passing a subsequent portion of the suture and a second cleat through the first object and the second object; and tensioning the suture so as to secure the suture to the second cleat.

13 Claims, 16 Drawing Sheets

(56) References Cited

U.S. PATENT DOCUMENTS

| | | | |
|---|---|---|---|
| 4,898,156 | A | 2/1990 | Gatturna et al. |
| 4,899,743 | A | 2/1990 | Nicholson et al. |
| 5,041,129 | A | 8/1991 | Hayhurst et al. |
| 5,269,809 | A | 12/1993 | Hayhurst et al. |
| 5,320,633 | A | 6/1994 | Allen et al. |
| 5,417,691 | A | 5/1995 | Hayhurst |
| 5,464,426 | A | 11/1995 | Bonutti |
| 5,522,846 | A | 6/1996 | Bonutti |
| 5,527,343 | A | 6/1996 | Bonutti |
| 5,549,631 | A | 8/1996 | Bonutti |
| 5,569,305 | A | 10/1996 | Bonutti |
| 5,584,862 | A | 12/1996 | Bonutti |
| 5,601,557 | A | 2/1997 | Hayhurst |
| 5,601,571 | A | 2/1997 | Moss |
| 5,647,874 | A | 7/1997 | Hayhurst |
| 5,718,717 | A | 2/1998 | Bonutti |
| 5,733,306 | A | 3/1998 | Bonutti |
| 5,782,862 | A | 7/1998 | Bonutti |
| 5,827,298 | A | 10/1998 | Hart et al. |
| 5,928,252 | A | 7/1999 | Steadman et al. |
| 5,941,439 | A | 8/1999 | Kammerer et al. |
| 6,033,430 | A | 3/2000 | Bonutti |
| 6,056,772 | A | 5/2000 | Bonutti |
| 6,066,160 | A * | 5/2000 | Colvin et al. ............... 606/232 |
| RE36,974 | E | 11/2000 | Bonutti |
| 6,312,448 | B1 | 11/2001 | Bonutti |
| 6,500,195 | B2 | 12/2002 | Bonutti |
| 6,506,197 | B1 | 1/2003 | Rollero et al. |
| 6,508,830 | B2 | 1/2003 | Steiner |
| 6,524,317 | B1 * | 2/2003 | Ritchart et al. ............... 606/232 |
| 6,635,073 | B2 | 10/2003 | Bonutti |
| 6,656,182 | B1 | 12/2003 | Hayhurst |
| 7,087,073 | B2 | 8/2006 | Bonutti |
| 7,153,312 | B1 | 12/2006 | Torrie et al. |
| 7,390,329 | B2 | 6/2008 | Westra et al. |
| 2002/0019649 | A1 | 2/2002 | Sikora et al. |
| 2002/0161401 | A1 | 10/2002 | Steiner |
| 2003/0130694 | A1 | 7/2003 | Bojarski et al. |
| 2004/0116963 | A1 | 6/2004 | Lattouf |
| 2004/0172046 | A1 | 9/2004 | Hlavka et al. |
| 2004/0243180 | A1 | 12/2004 | Donnelly et al. |
| 2005/0033363 | A1 | 2/2005 | Bojarski et al. |
| 2005/0080455 | A1 | 4/2005 | Schmieding et al. |
| 2005/0251210 | A1 | 11/2005 | Westra et al. |
| 2005/0283192 | A1 * | 12/2005 | Torrie et al. ............... 606/228 |
| 2006/0100627 | A1 | 5/2006 | Stone et al. |
| 2006/0189993 | A1 | 8/2006 | Stone |
| 2006/0247642 | A1 | 11/2006 | Stone et al. |
| 2006/0265009 | A1 | 11/2006 | Bonutti |
| 2006/0282085 | A1 | 12/2006 | Stone et al. |
| 2007/0185532 | A1 | 8/2007 | Stone et al. |
| 2007/0195532 | A1 | 8/2007 | Reisenauer et al. |
| 2008/0027446 | A1 | 1/2008 | Stone et al. |
| 2008/0065114 | A1 | 3/2008 | Stone et al. |
| 2008/0091219 | A1 | 4/2008 | Marshall et al. |
| 2009/0088797 | A1 | 4/2009 | Crombie et al. |
| 2010/0036395 | A1 | 2/2010 | Miller |
| 2010/0049212 | A1 | 2/2010 | Caborn et al. |
| 2011/0071549 | A1 | 3/2011 | Caborn et al. |

FOREIGN PATENT DOCUMENTS

| | | |
|---|---|---|
| WO | WO 2004/037094 | 5/2004 |
| WO | WO 2007/111986 | 10/2007 |
| WO | WO 2007/139785 | 12/2007 |
| WO | WO 2009/124215 | 10/2009 |

* cited by examiner

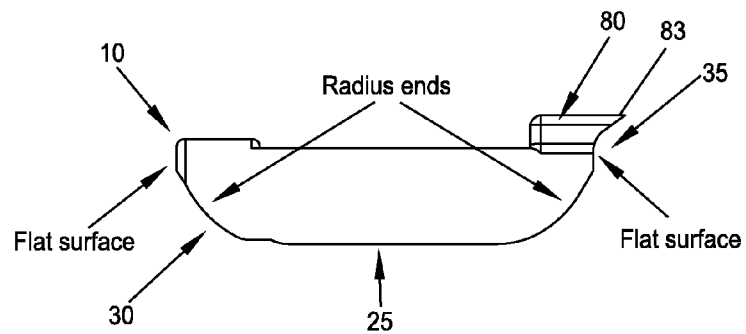
FIG. 8
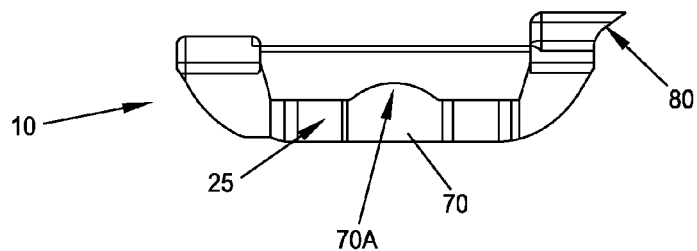
FIG. 9
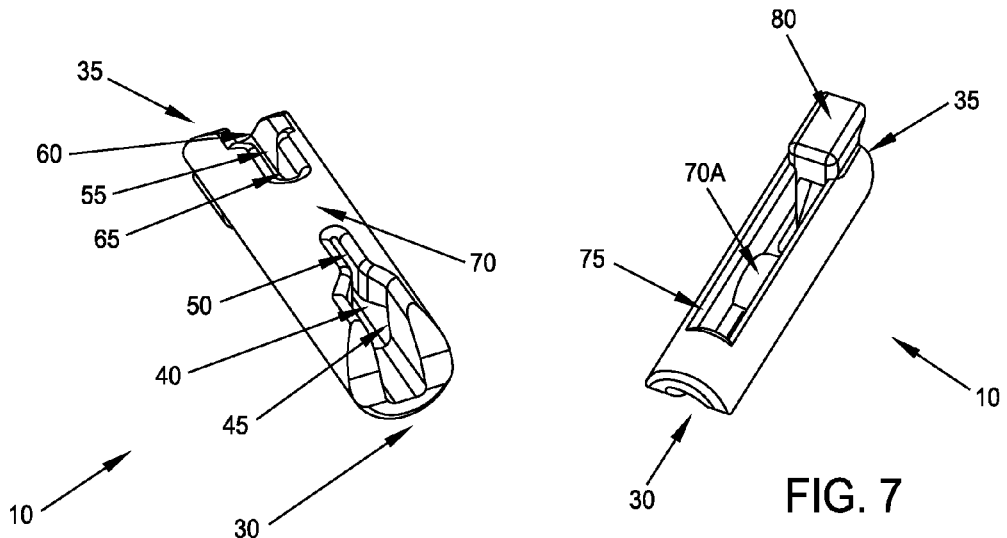
FIG. 10
FIG. 7

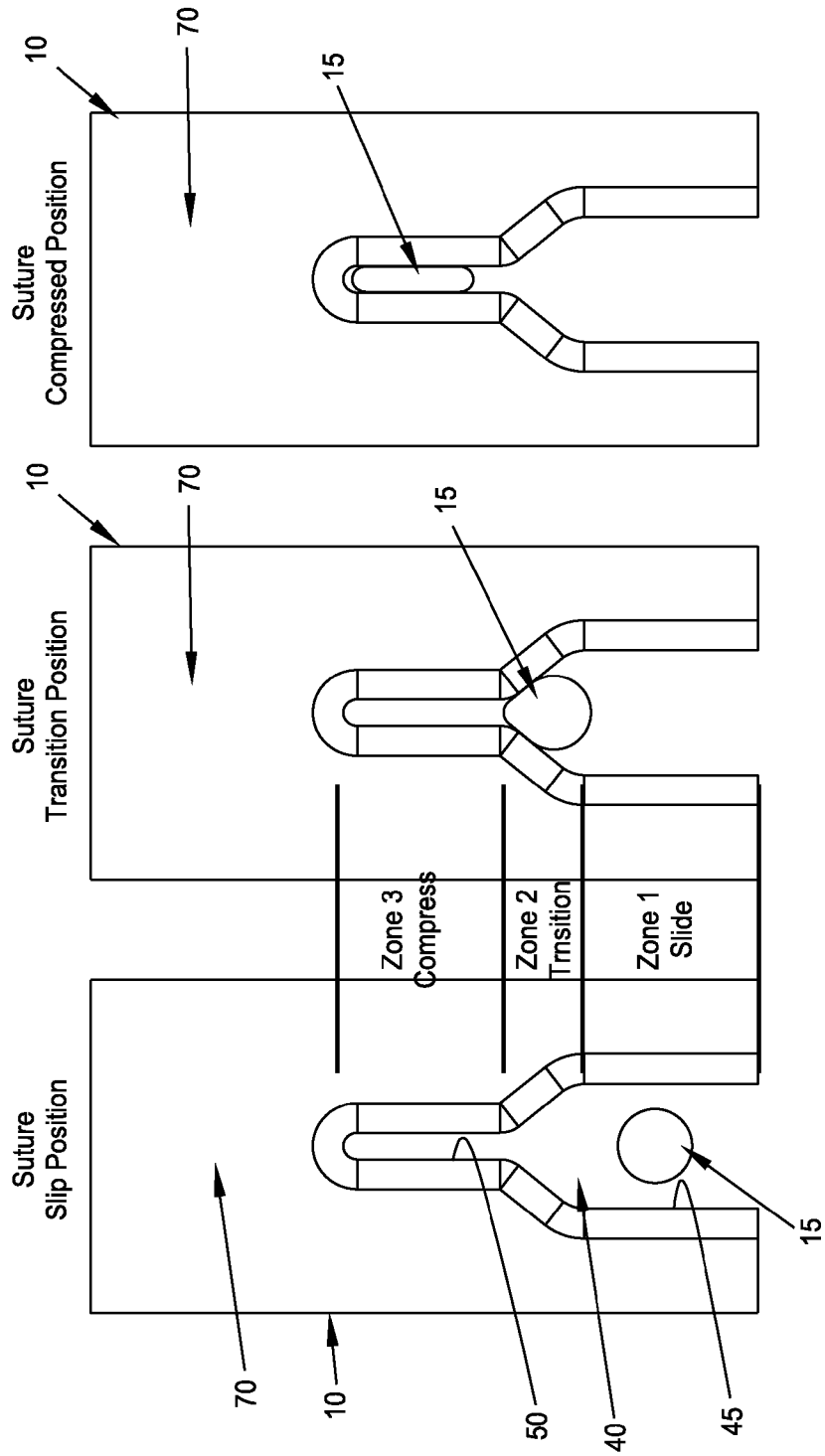

METHOD AND APPARATUS FOR MENISCAL REPAIR

REFERENCE TO PENDING PRIOR PATENT APPLICATION

This patent application is a continuation-in-part of pending prior U.S. patent application Ser. No. 12/417,571, filed Apr. 2, 2009 by David Caborn et al. for METHOD AND APPARATUS FOR MENISCAL REPAIR, which patent application claims benefit of:

(i) prior U.S. Provisional Patent Application Ser. No. 61/072,683, filed Apr. 2, 2008 by David Caborn et al. for MENISCAL REPAIR MAGAZINE CONCEPT;

(ii) prior U.S. Provisional Patent Application Ser. No. 61/135,149, filed Jul. 17, 2008 by David Caborn et al. for MENISCAL REPAIR PROVISIONAL 3; and (iii) prior U.S. Provisional Patent Application Ser. No. 61/208,294, filed Feb. 23, 2009 by Vincent Novak et al. for MENISCAL REPAIR PROVISIONAL 4.

The four (4) above-identified patent applications are hereby incorporated herein by reference.

FIELD OF THE INVENTION

This invention relates to surgical methods and apparatus in general, and more particularly to surgical methods and apparatus for the repair of the meniscus.

BACKGROUND OF THE INVENTION

The meniscus is a piece of cartilage located within the knee joint, between the top of the tibia and the bottom of the femur. The meniscus serves to facilitate stable movement of the tibia and femur relative to one another, and to absorb shock and to spread load.

The meniscus is frequently damaged (e.g., torn) as the result of injury and/or accident. A damaged meniscus can impede proper motion of the knee joint and cause pain, among other problems.

More particularly, the essential role of an intact meniscus, and its importance for proper knee function, has been well documented and accepted by the general orthopedic community. An intact and functioning meniscus is critical to optimally distribute weightbearing forces that transfer through the knee joint while maintaining knee stability. The meniscus is also vital to preserving the articular cartilage surfaces of the knee. Loss of meniscal tissue is considered to be a key precursor to the development of knee osteoarthritis.

A major challenge in repairing a torn meniscus is the fact that the tissue itself is a fibrous structure that is not uniformly vascular. The vascular zones of the meniscus comprise about one third of the meniscus tissue and are generally recognized as the "red-red" and "red-white" zones. The red-red zone (i.e., the most highly vascularized portion of the meniscus) is an area in which meniscal repairs are known to heal easily and is located along its outer periphery. The red-white zone extends from the most vascular area towards the inner portions of the meniscus where the blood supply eventually declines to non-vascular tissue (which is sometimes referred to as the "white-white" zone). It is believed that proper surgical technique is of great importance if a successful repair is to be achieved in the red-white zone. It is generally accepted knowledge that about 15% of all meniscal tears occur in the red-red zone, another 15% of meniscal tears occur in the red-white zone, and the remaining 70% of meniscal tears occur in the white-white (or non-vascularized) zone of the meniscus.

Another significant challenge in repairing a torn meniscus is that the size and shape of the tears vary, making the reduction and apposition of the torn tissue difficult to accomplish. Without proper apposition and stability, torn meniscal tissue will not heal properly.

The art of repairing torn meniscal tissue was first developed and pioneered throughout the 1980's by early sports medicine-focused surgeons. The earliest methods employed only suture in the repair. The techniques of "inside-out" and "outside-in" suturing became the so-called "gold standard" for the repair of meniscal tissue. Both of these techniques focused on passing small diameter suture (size 2-0 or 3-0) through the meniscus, reducing and closing the tear, and then tying a suture knot over the knee capsule so as to fixate and stabilize the tear. A feature of these early all-suture repairs was that the surface of the meniscus was kept relatively smooth since the suture knot was outside of the knee joint, and the use of a needle and suture allowed the surgeon a great deal of flexibility in adequately reducing and stabilizing the tear. Eventually, these early surgeons began concomitant use of complementary techniques to promote a vascular response in the more non-vascular areas of the meniscus. Methods such as tear edge and meniscapsular rasping, the application of an interpositional blood clot, trephination to create a vascular channel, and fascial sheath or synovial flap coverage have been shown in several studies to be 150% more effective in healing a torn meniscus when compared to repairs that do not use such concomitant techniques.

The specific issues and challenges associated with the aforementioned all-suture inside-out and outside-in repair techniques are centered primarily on issues relating to the "user interface" and to the "tethering" of the meniscus to the knee capsule. More particularly, the "user interface" issues generally relate to the technical demands required in the operating room: the skill of the surgeon and the number of assistants required to safely pass the needle and suture from the anterior portion of the meniscus through the posterior portion of the meniscus and exit out through the posterior/medial aspect of the knee joint (i.e., the so-called "inside-out" technique); or the passing of a needle and suture from the medial aspect of the exterior of the knee into the knee joint, through the meniscus, the retrieval and re-insertion back into the meniscus, and then passage back out through the capsule to the medial aspect of the knee (i.e., the so-called "outside-in" technique). In addition, the execution of a complementary technique to promote a sustained vascular response is left to the ingenuity of the surgeon. The aforementioned tethering issues relate to more recent concerns about fixating suture over the knee capsule and thereby "tethering" the meniscus to the knee capsule, since evidence suggests that such tethering of the meniscus to the knee capsule may interfere with the normal biomechanics of the meniscus (e.g., load and force distribution, etc.).

As recognition of the importance of the meniscus grew in the late 1980's, new methods of meniscus repair were developed. These new methods focused on improving execution of the procedure in order to make it easier, simpler and faster to accomplish. The new gold standard approach became the so-called "all-inside" technique. The all-inside technique is intended to not violate the knee capsule or require any incisions on the posterior/medial aspects of the knee (i.e., such as is required with the inside-out and outside-in suturing techniques discussed above). With the all-inside technique, the entire repair—both approximation and fixation—is performed intra-articularly.

The first all-inside repair devices were tack-like implants that were inserted through a standard arthroscopic portal and then forcefully pushed through the meniscus, crossing through the tear, thereby closing and fixing the tear without the use of suture. These tack-like implants were formed out of biomaterials such as PLA, PLLA or PGA that were expected to biodegrade over time. However, these materials are quite hard when first inserted into the meniscus and, in use, were found to degrade or bioabsorb much more slowly than anticipated. Clinical use and follow-up have demonstrated the inherent risks associated with the use of such tack-like implants within the knee joint, as numerous published studies have reported device failure which can lead to tear reformation, loose implants within the knee joint and articular cartilage damage. Furthermore, it can be challenging for the surgeon to adequately address various tear shapes and sizes using these tack-like implants.

As a result, attention has returned to suture-based repairs, with a new focus on performing a suture-based repair using an all-inside technique. There are several recent systems that seek to accomplish this goal. However, none of these systems have been found to be completely satisfactory.

Thus, there is a need for a new and improved method and apparatus for meniscal repair.

SUMMARY OF THE INVENTION

The present invention provides a new and improved method and apparatus for meniscal repair.

In one form of the present invention, there is provided a cleat for securing suture to tissue, the cleat comprising:
  an elongated body having a distal end and a proximal end, the distal end having a distal slot extending proximally into the elongated body, and the proximal end having a proximal slot extending distally into the body;
  the distal slot comprising a wide section and a narrow section, wherein the wide section has a width such that the suture is slidably accommodated therein and the narrow section has a width such that the suture is bound therein, and further wherein the wide section is disposed distally of the narrow section.

In another form of the present invention, there is provided a system comprising:
  a suture;
  at least one cleat, the cleat comprising:
    an elongated body having a distal end and a proximal end, the distal end having a distal slot extending proximally into the elongated body, and the proximal end having a proximal slot extending distally into the body;
    the distal slot comprising a wide section and a narrow section, wherein the wide section has a width such that the suture is slidably accommodated therein and the narrow section has a width such that the suture is bound therein, and further wherein the wide section is disposed distally of the narrow section;
  wherein the suture is initially disposed within the wide section of the distal slot of the at least one cleat so that the suture is slidable relative to the at least one cleat.

In another form of the present invention, there is provided a fastening construct comprising:
  a suture;
  a leading cleat, the suture being connected to the leading cleat so that the leading cleat can restrict retrograde movement of the suture relative to the leading cleat;
  at least one trailing cleat, the at least one trailing cleat comprising:
    an elongated body having a distal end and a proximal end, the distal end having a distal slot extending proximally into the elongated body, and the proximal end having a proximal slot extending distally into the body;
    the distal slot comprising a wide section and a narrow section, wherein the wide section has a width such that the suture is slidably accommodated therein and the narrow section has a width such that the suture is bound therein, and further wherein the wide section is disposed distally of the narrow section;
  wherein the suture is initially disposed within the wide section of the distal slot of the at least one trailing cleat so that the suture is slidable relative to the at least one trailing cleat; and
  wherein the suture is thereafter placed under tension and disposed within the narrow section of the distal slot so as to bind the suture under tension to the at least one trailing cleat, the binder of the suture under tension to the at least one trailing cleat being independent of suture disposed beyond the at least one trailing cleat.

In another form of the present invention, there is provided a method for securing a first element to a second element, the method comprising the steps of:
  providing a system comprising:
    a suture;
    at least two cleats, each cleat comprising:
      an elongated body having a distal end and a proximal end, the distal end having a distal slot extending proximally into the elongated body, and the proximal end having a proximal slot extending distally into the body;
      the distal slot comprising a wide section and a narrow section, wherein the wide section has a width such that the suture is slidably accommodated therein and the narrow section has a width such that the suture is bound therein, and further wherein the wide section is disposed distally of the narrow section;
    wherein the suture is initially disposed within the wide section of the distal slot of each of the at least two cleats so that the suture is slidable relative to the at least two cleats; and
  an inserter, the inserter comprising a hollow elongated shaft having a sharp point disposed eccentric to the longitudinal axis of the hollow elongated shaft, and further wherein the suture and the at least two cleats are disposed within the lumen of the hollow elongated shaft;
  passing the inserter through the first object and the second object so that the sharp point of the inserter resides on the far side of the second object;
  ejecting the first cleat on the far side of the second object;
  withdrawing the inserter out of the first object and the second object;
  tensioning the suture so that the suture is drawn into the narrow section of the distal slot of the first cleat, whereby to bind the suture to the first cleat;
  moving the inserter to another location on the first object;
  passing the inserter back through the first object and the second object so that the sharp point of the inserter resides on the far side of the second object;
  ejecting the second cleat on the far side of the second object;
  withdrawing the inserter out of the first object and the second object; and tensioning the suture so that the suture is drawn into the narrow section of the distal slot of the second cleat, whereby to bind the suture to the second cleat.

In another form of the present invention, there is provided a method for securing a first element to a second element, the method comprising the steps of:
  providing a system comprising:
    a suture;
    a leading cleat, the suture being connected to the leading cleat so that the leading cleat can restrict retrograde movement of the suture relative to the leading cleat;
    a trailing cleat, the trailing cleat comprising:
      an elongated body having a distal end and a proximal end, the distal end having a distal slot extending proximally into the elongated body, and the proximal end having a proximal slot extending distally into the body;
      the distal slot comprising a wide section and a narrow section, wherein the wide section has a width such that the suture is slidably accommodated therein and the narrow section has a width such that the suture is bound therein, and further wherein the wide section is disposed distally of the narrow section;
    wherein the suture is initially disposed within the wide section of the distal slot of the trailing cleat so that the suture is slidable relative to the trailing cleat; and
    an inserter, the inserter comprising a hollow elongated shaft having a sharp point, and further wherein the suture, the leading cleat and the trailing cleat are disposed within the lumen of the hollow elongated shaft;
  passing the inserter through the first object and the second object so that the sharp point of the inserter resides on the far side of the second object;
  ejecting the leading cleat on the far side of the second object;
  withdrawing the inserter out of the first object and the second object;
  moving the inserter to another location on the first object;
  passing the inserter back through the first object and the second object so that the sharp point of the inserter resides on the far side of the second object;
  ejecting the trailing cleat on the far side of the second object;
  withdrawing the inserter out of the first object and the second object; and
  tensioning the suture so that the suture is drawn into the narrow section of the distal slot of the second cleat, whereby to bind the suture to the second cleat.

In another form of the present invention, there is provided a method for securing a first object to a second object, the method comprising:
  providing a suture and a plurality of cleats slidably mounted on the suture;
  passing one end of the suture and a first cleat through the first object and the second object;
  tensioning the suture so as to secure the suture to the first cleat;
  passing a subsequent portion of the suture and a second cleat through the first object and the second object; and
  tensioning the suture so as to secure the suture to the second cleat.

In another form of the present invention, there is provided a method for securing a first object to a second object, the method comprising:
  providing a suture, a leading cleat connected to the suture, and a plurality of trailing cleats slidably mounted on the suture;
  passing one end of the suture and the leading cleat through the first object and the second object at a first location;
  passing a subsequent portion of the suture and a first trailing cleat through the first object and the second object at a second location, the second location being displaced from the first location;
  tensioning the suture so as to secure the suture to the first trailing cleat, whereby to create a first stable fastening construct by means of the leading cleat, the first trailing cleat and the suture tensioned therebetween;
  passing another subsequent portion of the suture and a second trailing cleat through the first object and the second object at a third location, the third location being displaced from the second location; and
  tensioning the suture so as to secure the suture to the second trailing cleat, whereby to create a second stable fastening construct by means of the first trailing cleat, the second trailing cleat and the suture tensioned between.

BRIEF DESCRIPTION OF THE DRAWINGS

These and other objects and features of the present invention will be more fully disclosed or rendered obvious by the following detailed description of the invention, which is to be considered together with the accompanying drawings wherein like numbers refer to like parts, and further wherein:

FIGS. 7-10, 10A, 10B, 10C, 10D, 10E and 10F are schematic views showing further details of a cleat of the meniscal repair system shown in FIGS. 1-3;

DETAILED DESCRIPTION OF THE INVENTION

Figure 1:
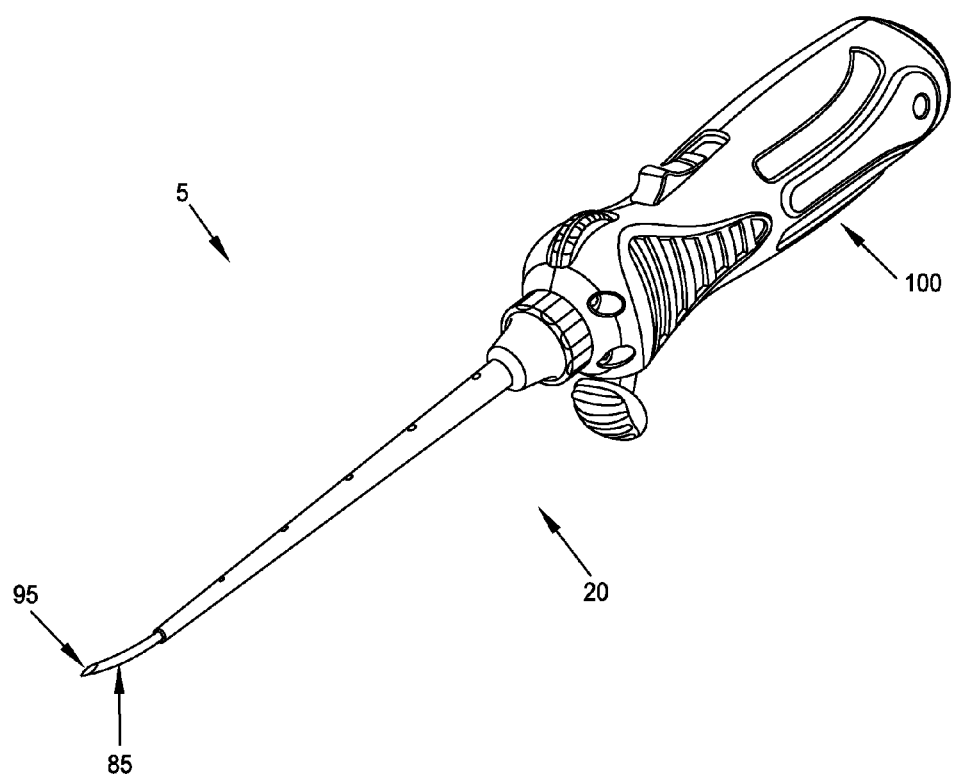
FIGS. 1-3 are schematic views showing a meniscal repair system formed in accordance with the present invention.
Figure 2:
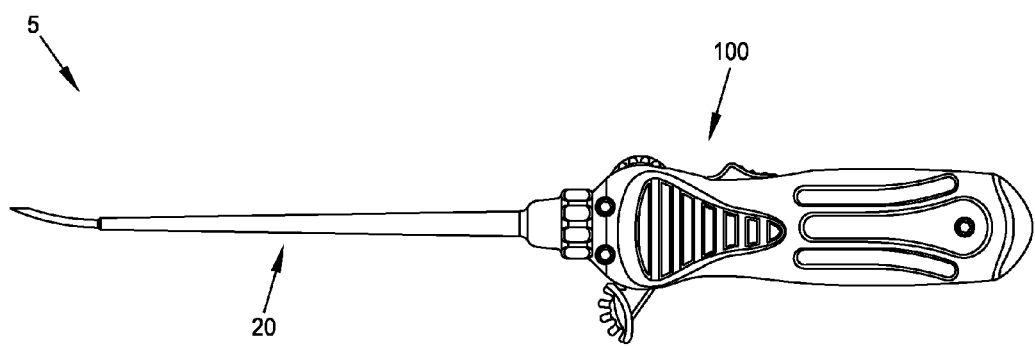
Figure 3:
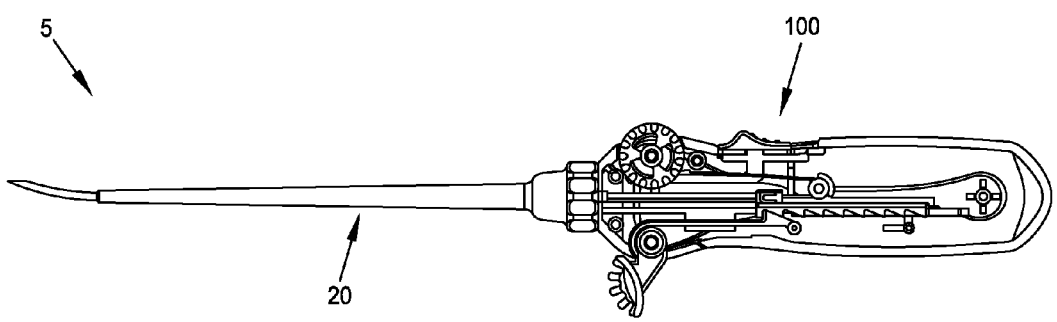

Looking first at FIGS. 1-6, there is shown a novel system 5 for meniscal repair. System 5 generally comprises a plurality of cleats 10, a length of suture 15 and an inserter 20.

Cleats 10 are shown in greater detail in FIGS. 7-10, 10A, 10B, 10C, 10D, 10E and 10F. Each of the cleats 10 generally comprises an elongated body 25 which, in its preferred construction, is generally cylindrical so that it can make a close sliding fit within the lumen of a hollow delivery needle, as will hereinafter be discussed in further detail. Elongated body 25 is characterized by a distal end 30 and a proximal end 35.

On a "bottom" side of elongated body 25, a distal slot 40 extends proximally along the elongated body, with distal slot 40 comprising a wide section 45 and a narrow section 50. Also on the "bottom" side of elongated body 25, a proximal slot 55 extends distally along the elongated body, with proximal slot 55 comprising a wide section 60 and a narrow section 65. Distal slot 40 is aligned with proximal slot 55.

Preferably narrow section 50 of distal slot 40 is narrower than narrow section 65 of proximal slot 55 (FIG. 10), and preferably wide section 45 of distal slot 40 is the same width as wide section 60 of proximal slot 55. Thus it will be seen that narrow section 50 of distal slot 40 is narrower than narrow section 65 of proximal slot 55, which is itself narrower than the wide section 45 of distal slot 40 and wide section 60 of proximal slot 55.

Figure 10A:
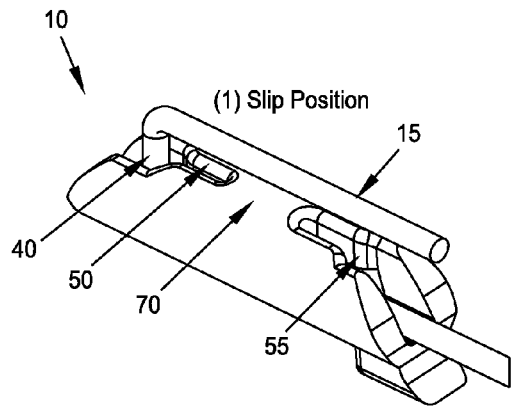
Figure 10B:
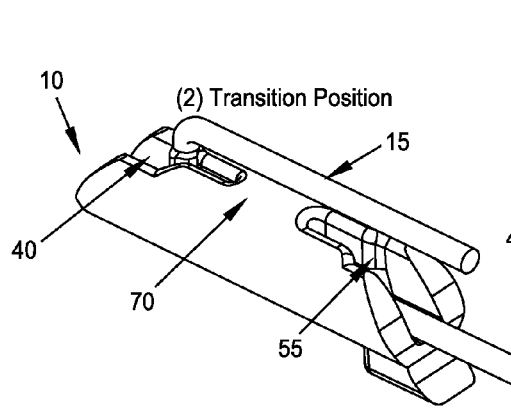
Figure 10C:
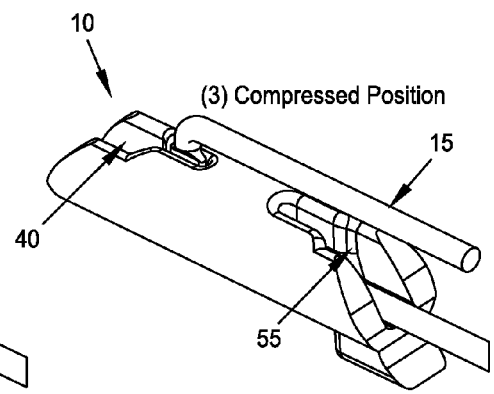
Figure 11:
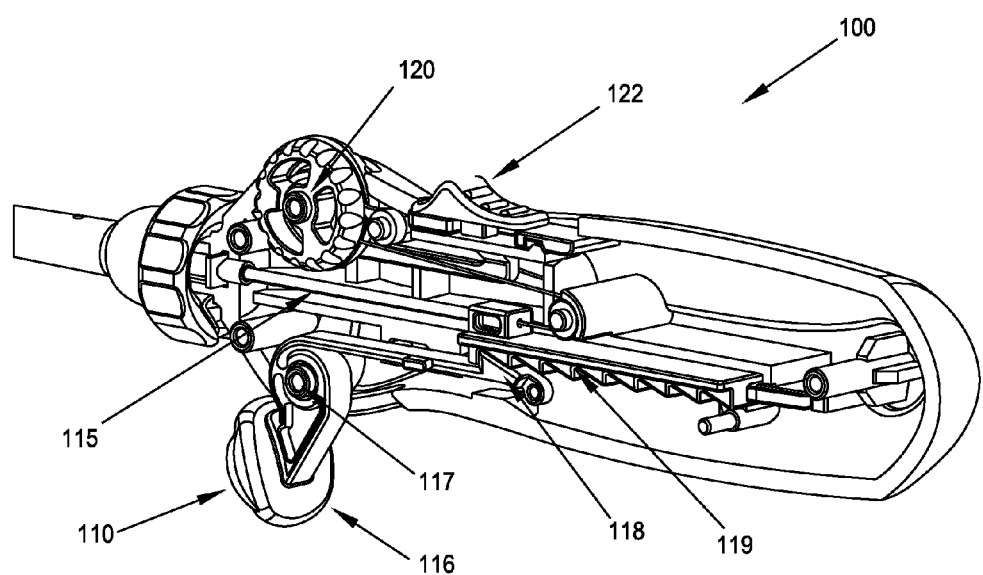
FIGS. 11-13 are schematic views showing further details of the handle of the meniscal repair system shown in FIGS. 1-3.
Figure 12:
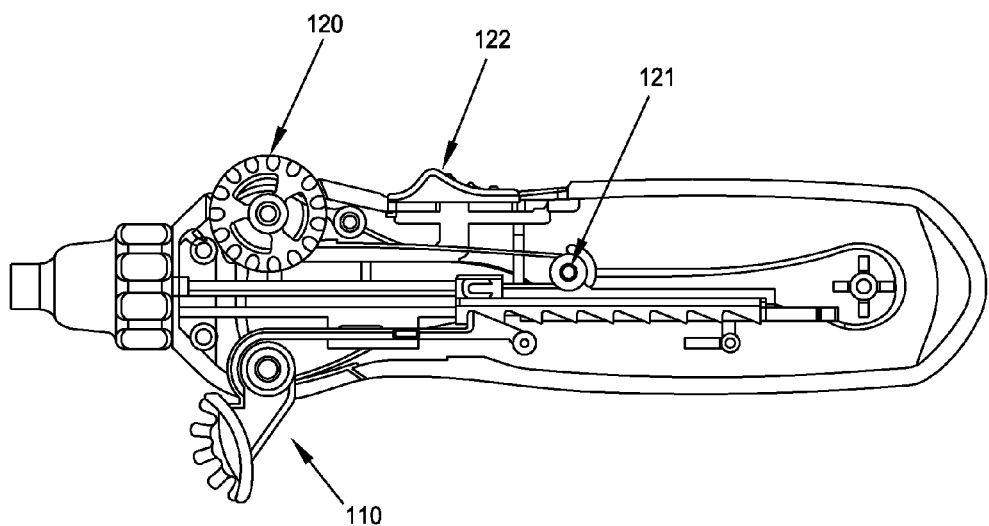
Figure 13:
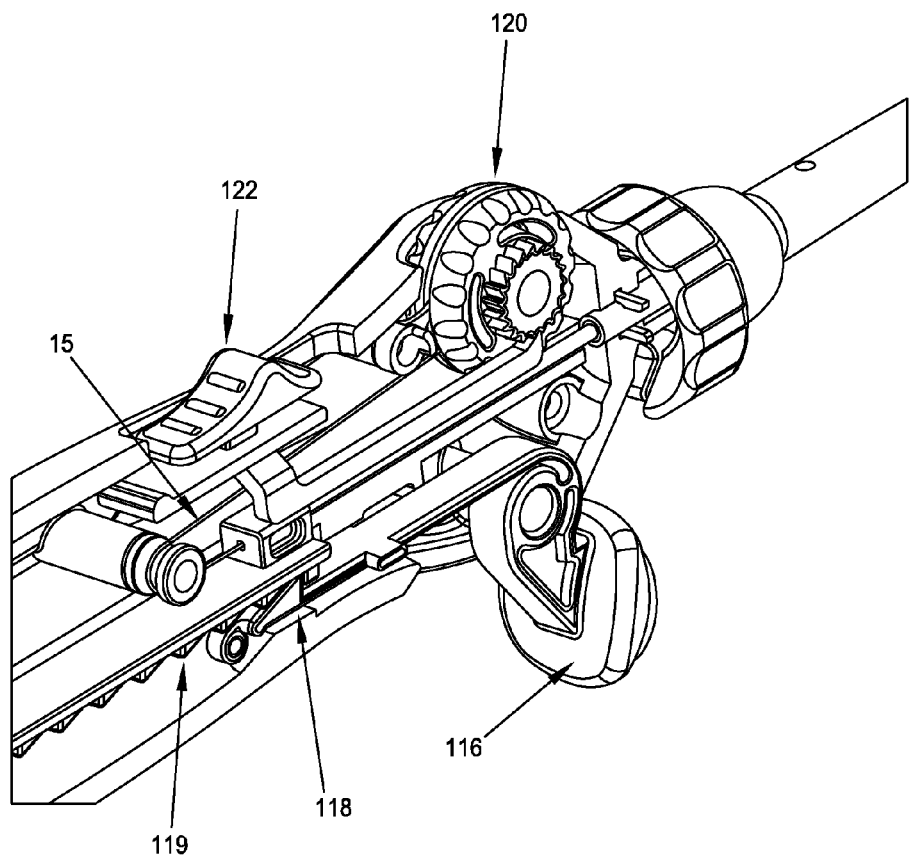

Furthermore, the aforementioned narrow section 50, narrow section 65, wide section 45 and wide section 60 are sized relative to suture 15 so that: (i) suture 15 will make a tight binding fit with narrow section 50 of distal slot 40, (ii) suture 15 will make a sliding fit with narrow section 65 of proximal slot 55, and (iii) suture 15 will move easily through wide section 45 of distal slot 40 and wide section 60 of proximal slot 55. See also FIGS. 10A-10F: in FIGS. 10A and 10D, suture 15 is shown moving easily through wide section 45 of distal slot 40; in FIGS. 10B and 10E, suture 15 is shown in a transition state as it moves from wide section 45 of distal slot 40 to narrow section 50 of distal slot 40; and FIGS. 10C and 10F show suture 15 compressed and bound within narrow section 50 of distal slot 40. A wall 70 separates narrow section 50 of distal slot 40 from narrow section 65 of proximal slot 55.

On a "top" side of elongated body 25 (i.e., on the side diametrically opposed to the aforementioned "bottom" side of elongated body 25), a recess 75 (FIG. 7) extends into elongated body 25. Thus, recess 75 is diametrically opposed to the aforementioned distal slot 40 and proximal slot 55. Recess 75 is formed long enough, and deep enough, so that it communicates with narrow section 50 of distal slot 40 and with a portion of wide section 45 of distal slot 40, and it communicates with narrow section 65 of proximal slot 55 and with a portion of wide section 60 of proximal slot 55 (FIGS. 7, 9 and 10). Recess 75 is significantly wider than suture 15, so that suture 15 can move easily through recess 75.

By forming recess 75 as a wide opening on the "top" side of the cleat (i.e., the side of the cleat diametrically opposite to distal slot 40, proximal slot 55 and wall 70), wall 70 can be increased in thickness (e.g., as shown at 70A) so as to reinforce the bridge of material that separates the distal edge of proximal slot 55 and the proximal edge of distal slot 40. This ability to increase the thickness of wall 70 at location 70A is made possible because cleat 10 is not a tubular structure—if cleat 10 were in the form of a tubular structure, increasing the thickness of wall 70 at location 70A would cause the internal diameter of the cleat to be reduced at that location, which could cause suture 15 to bind within the body of the cleat. With the present construction, by having an open "roof" (i.e., the wide recess 75), the suture can ride over the bump at location 70A and protrude through recess 75, thereby allowing the suture to slide easily through the cleat body, even where wall 70 is increased in thickness.

On account of the foregoing construction, wide section 45 of distal slot 40, narrow section 50 of distal slot 40, recess 75, wide section 60 of proximal slot 55 and narrow section 65 of proximal slot 55 provide a suture pathway about elongated body 25 of cleat 10. Furthermore, and as will hereinafter be discussed in further detail, on account of the disposition and sizing of the aforementioned wide section 45, narrow section 50, recess 75, wide section 60 and narrow section 65, cleat 10 can be slidably mounted on suture 15 and then selectively secured to the suture.

A fin 80 extends "upwardly" out of the "top" side of elongated body 25 (FIGS. 7-9). Fin 80 is aligned with recess 75 and diametrically opposed to distal slot 40 and proximal slot 55. Fin 80 can be provided with a sharp edge 83 at its proximal end if desired.

It should be appreciated that, while elongated body 25 is preferably generally cylindrical, it is also preferably not tubular: at no point along its length does elongated body 25 have a complete outer periphery with a hollow interior.

Suture 15 (FIG. 6) may comprise any appropriate suture material of the sort known in the art. By way of example but not limitation, suture 15 may comprise braided suture, so-called "monofilament" suture, etc., and may be formed so as to be either "permanent" or absorbable. In one preferred form of the invention, suture 15 comprises braided suture.

As will hereinafter be discussed in further detail, suture 15 is intended to be passed through cleat 10 (or, stated another way, cleat 10 is intended to be "strung" onto suture 15) by passing the suture through distal slot 40, into and along top recess 75, and back through proximal slot 55 (see FIG. 6). In this respect it will be appreciated that wide section 45 of distal slot 40, recess 75 and wide section 60 of proximal slot 55 are all sized sufficiently wide relative to suture 15 that suture 15 can slide easily through those openings. Thus, so long as suture 15 remains disposed in those openings (i.e., while cleat 10 is disposed inside inserter 20, as will hereinafter be discussed), suture 15 will be free to move easily through cleat 10 (and, correspondingly, cleat 10 will be free to slide easily along suture 15). However, and as will hereinafter be discussed in further detail, when suture 15 is directed into narrow section 50 of distal slot 40, a tight interference fit will be created between the cleat and the suture, in a cleating action, thereby securing the cleat and suture to one another (i.e., after deployment within the body of the patient).

As will also hereinafter be discussed in further detail, a plurality of cleats 10 may be "strung" on a single suture 15 (see FIG. 6). As noted above, when suture 15 passes through wide section 45 of distal slot 40, recess 75 and wide section 60 of proximal slot 55 of each cleat 10, the cleats may be advanced along the suture. However, and as will hereinafter be discussed in further detail, when suture 15 is directed into narrow section 50 of distal slot 40 of a cleat 10, a tight interference fit will be created between that cleat and the suture, thereby securing that cleat and the suture to one another. Significantly, and as will hereinafter be discussed in further detail, when a plurality of cleats 10 are slidably mounted on a single suture 15, each of the cleats 10 may be selectively and individually secured to the suture when and where desired by the user, thereby allowing the user to independently adjust the degree of tension between each of the cleats.

Figure 4:
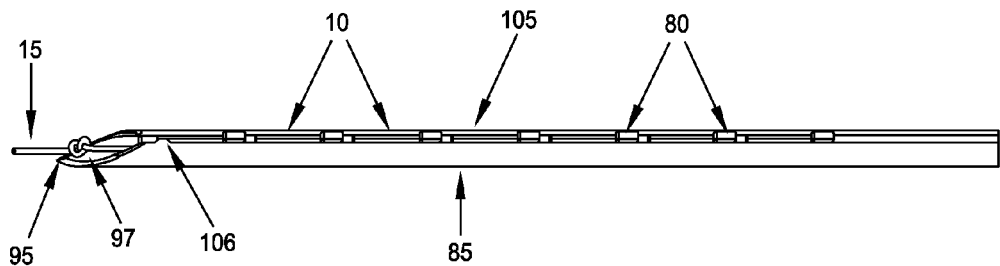
FIGS. 4-6 are schematic views showing the distal end of the meniscal repair system shown in FIGS. 1-3.
Figure 5:
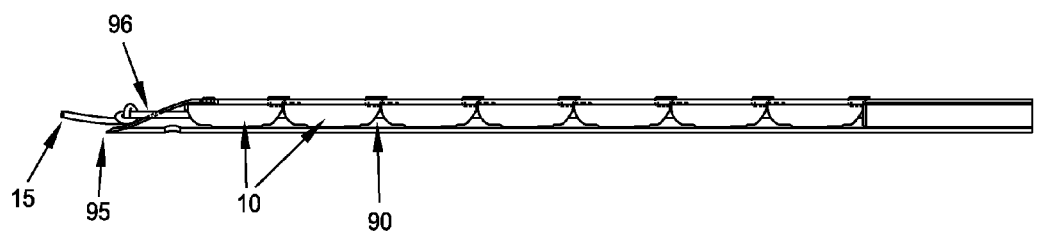
Figure 6:
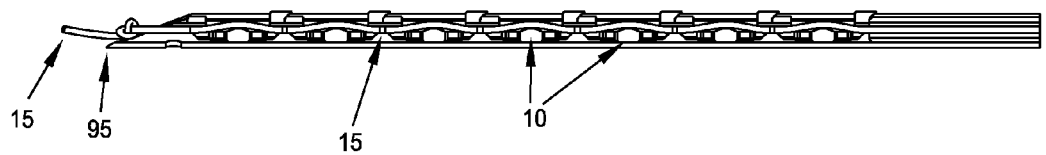

Preferably suture 15 is knotted off distal to the distal most cleat 10 in elongated shaft 85 (FIGS. 4-6).

Looking again at FIGS. 1-6, inserter 20 generally comprises an elongated shaft 85 having a central lumen 90 extending therethrough. Elongated shaft 85 terminates in a sharp point 95 at its distal end. Sharp point 95 is created by forming an oblique face 96 (FIGS. 4-6) on the distal end of the elongated shaft, such that a section 97 of elongated shaft 85 is exposed at the mouth of lumen 90. A handle 100 (FIGS. 1-3) is secured to elongated shaft 85 at its proximal end. A slot 105 (FIG. 4) is formed in elongated shaft 85 on its "top" side. Slot 105 extends all the way to the distal tip of elongated shaft 85. A small projection 106 (FIG. 4) extends into slot 105.

As seen in FIGS. 4-6, elongated shaft 85 is sized to receive a plurality of cleats 10 therein, with those cleats being "strung" on a single suture 15. To this end, lumen 90 of elongated shaft 85 is sized to slidably receive elongated bodies 25 of cleats 10, with fins 80 of cleats 10 extending out through slot 105 of elongated shaft 85. Fins 80 and slot 105 cooperate to keep cleats 10 aligned within lumen 90 of elongated shaft 85. The aforementioned small projection 106 provides nominal resistance to the passage of fins 80 through slot 105. Small projection 106 is positioned such that the lead cleat 10 in lumen 90 normally does not exit the distal end of the elongated shaft; however, with the application of a distally-directed force, fin 80 can slip past small projection 106 so as to release the lead cleat from lumen 90. Thus, small projection 106 essentially acts as a gate for the selective release of cleats 10 from elongated shaft 85.

It will be appreciated that, due to the construction and sizing of cleats 10 and suture 15, suture 15 cannot become bound to the cleat while the cleats are inside elongated shaft 85—the suture can only become bound to a cleat after that cleat has been ejected from the elongated shaft, as will hereinafter be discussed in further detail.

Preferably, handle 100 (FIGS. 1-3 and 11-13) includes a trigger mechanism 110 for selectively advancing a drive shaft 115 along lumen 90 of elongated shaft 85, whereby to selectively advance cleats 10 along lumen 90 and thereby eject cleats 10 one at a time from the distal end of elongated shaft 85. Trigger mechanism 110 preferably comprises a ratchet mechanism for selectively advancing drive shaft 115. In one preferred form of the invention, trigger mechanism 110 comprises a trigger 116 which is pivotally mounted on a pivot pin 117 for reciprocally moving a finger 118 relative to a rack 119. Rack 119 is connected to the proximal end of drive shaft 115. As a result of this construction, when trigger 116 is pulled, rack 119 (and hence drive shaft 115) is moved distally. By forming trigger 116 out of a polymer material with a spring return, trigger 116 returns to its starting position after each throw. Alternatively, a spring mechanism (not shown) can be used to return trigger 116 to its starting position after each throw. Preferably trigger mechanism 110 is set for a small "overthrow", such that when trigger 116 is pulled, drive shaft 115 moves slightly further distally than is required to eject a cleat from the distal end of elongated shaft 85, whereby to ensure that the cleat is completely expelled from the distal end of elongated shaft 85, as will hereinafter be discussed in further detail.

Handle 100 preferably also includes a suture spool 120 for holding a supply of suture emerging from the proximal-most cleat 10 which is held in lumen 90 of elongated shaft 85. To this end, drive shaft 115 is preferably hollow, or otherwise shaped, so that suture 15 can extend from the proximal-most cleat 10, through drive shaft 115, around a pulley 121 and up into suture spool 120. A thumb lock 122 permits suture spool 120 to be selectively locked against rotation, so that tension can be selectively applied to the suture 15 extending through drive shaft 115 and cleats 10, as will hereinafter be discussed in further detail.

Figure 14:
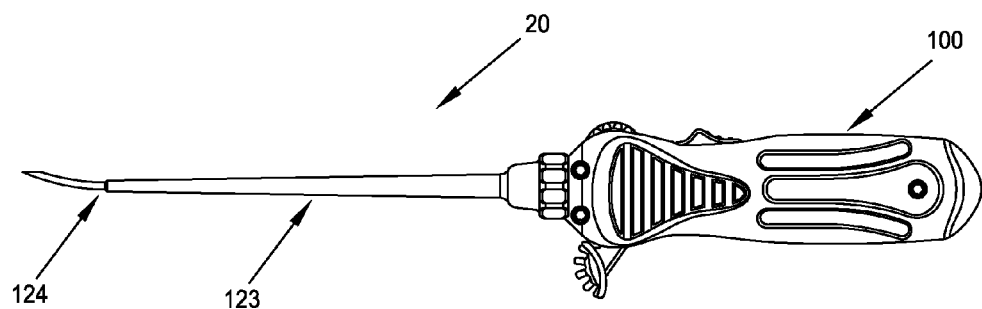
FIGS. 14-16 are schematic views showing further details of a penetration limiting means of the meniscal repair system of FIGS. 1-3.
Figure 15:
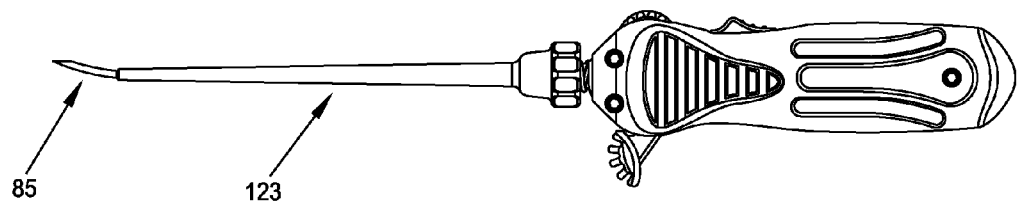
Figure 16:
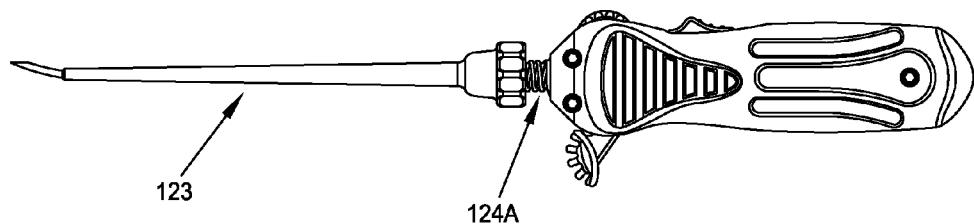

Preferably inserter 20 also includes means for limiting penetration of elongated shaft 85 into tissue. More particularly, a sleeve 123 (FIGS. 14-16) having a stop surface 124 at its distal end is adjustably mounted on elongated shaft 85, e.g., using mating screw threads 124A, such that the position of stop surface 124 vis-à-vis elongated shaft 85 can be set by rotating sleeve 123 on elongated shaft 85.

Alternatively, if desired, other means may be used to limit penetration of elongated shaft 85 into tissue. By way of example but not limitation, screw-mounted sleeve 123 may be replaced by a snap-on component. In this form of the invention, the user could select a snap-on component of a selected size from a kit having a selection of differently-sized snap-on components, and attach the snap-on component to the inserter, whereby to regulate penetration of elongated shaft 85 into tissue.

Figure 17:
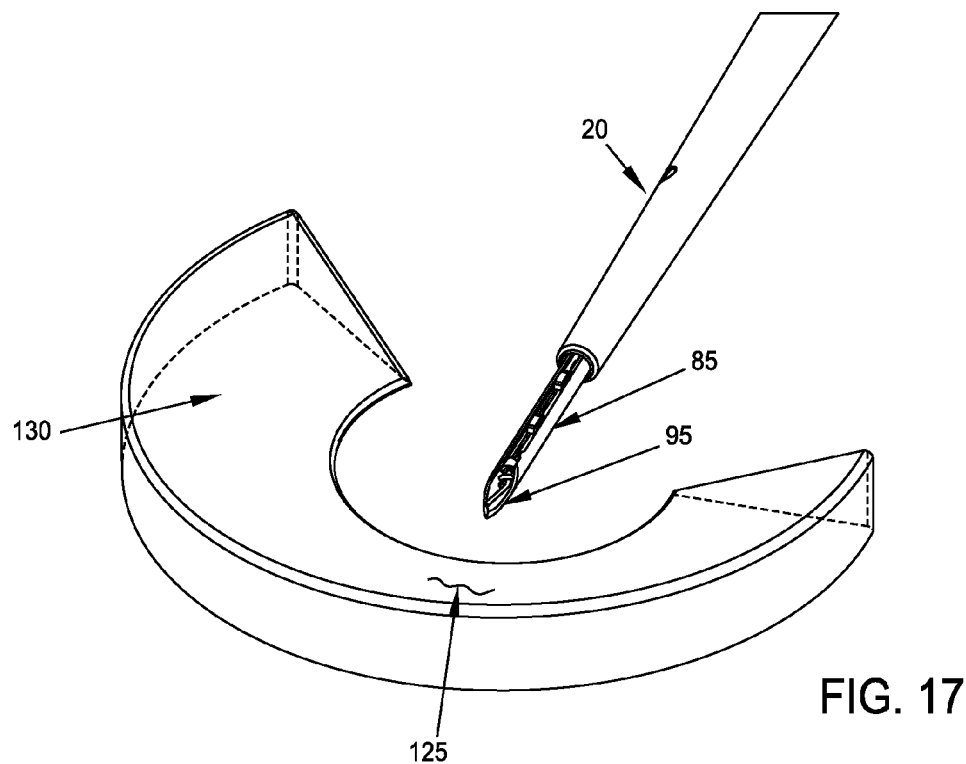
FIGS. 17-31 are schematic views showing a meniscal repair effected using the system shown in FIGS. 1-3.
Figure 18:
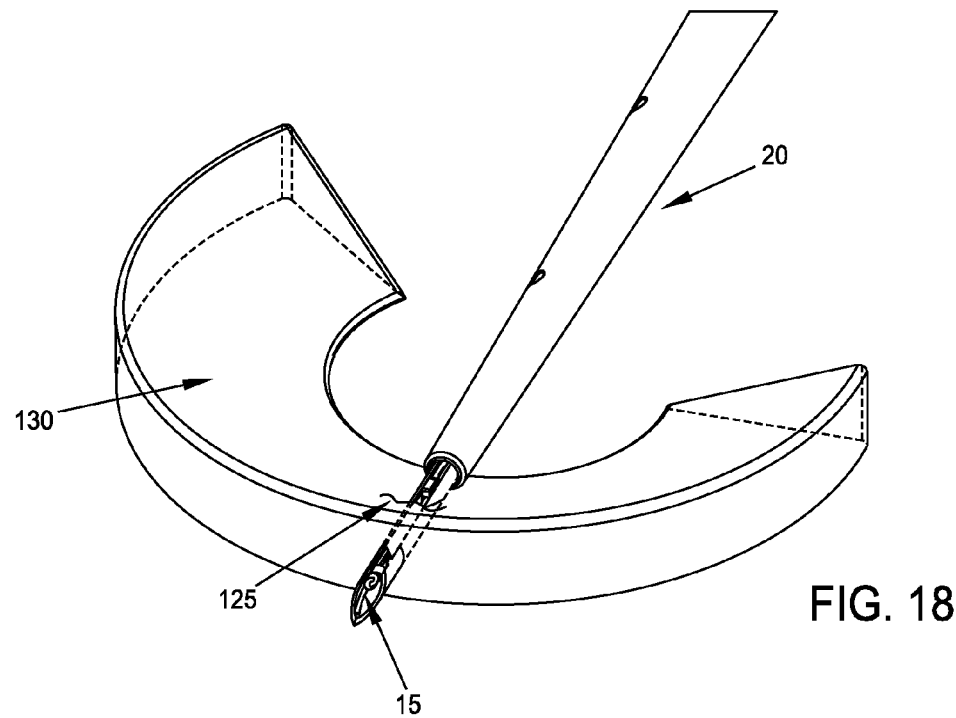
Figure 19:
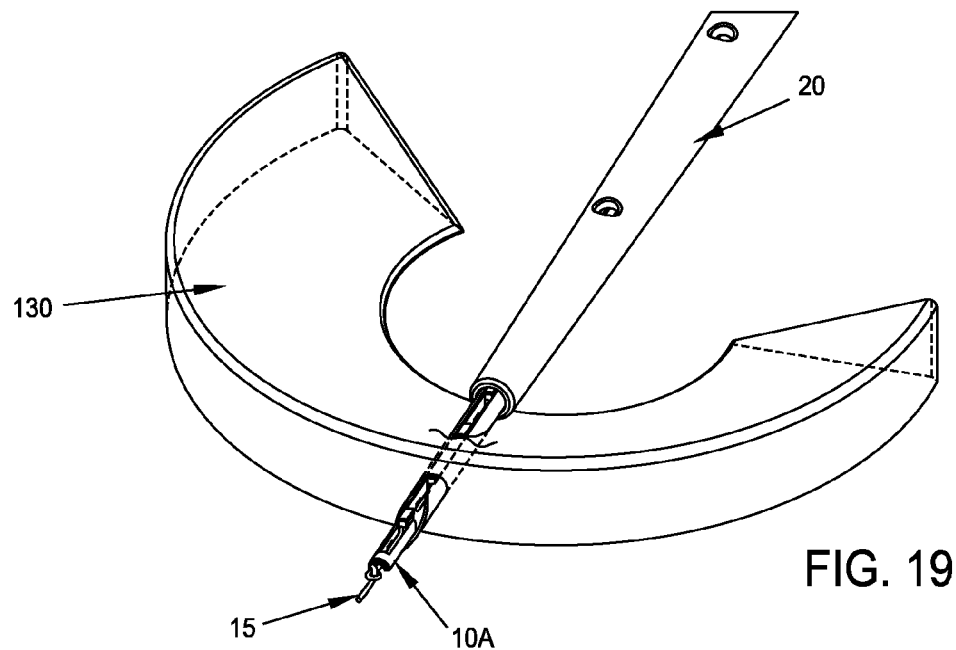

As seen in FIGS. 17-31, system 5 may be used to close a tear 125 in a meniscus 130 using a plurality of cleats 10 and a suture 15. More particularly, sharp point 95 of elongated shaft 85 is advanced into meniscus 130, across tear 125, and then out the far side of meniscus 130 (FIGS. 17 and 18). Then the leading cleat 10 in lumen 90 (i.e., cleat 10A in FIG. 19) is ejected from elongated shaft 85. This is done by advancing drive shaft 115 (e.g., with trigger mechanism 110) so that the leading cleat 10 has its fin 80 forced past small projection 106 in slot 105, whereby to release the cleat from the inserter. It should be appreciated that, due to the slight overthrow of drive shaft 115, it will be ensured that the cleat will be completely expelled from the distal end of elongated shaft 85. It should also be appreciated that, due to the slight overthrow of drive shaft 115, the next cleat in elongated shaft 85 may start to partially emerge from elongated shaft 85. However, this cleat will be free to slide back into lumen 90 of elongated shaft 85 if and when the cleat subsequently engages tissue so that it is elongated shaft 85, and not the cleats, which resist the forces imparted by the tissue during tissue penetration.

Figure 20:
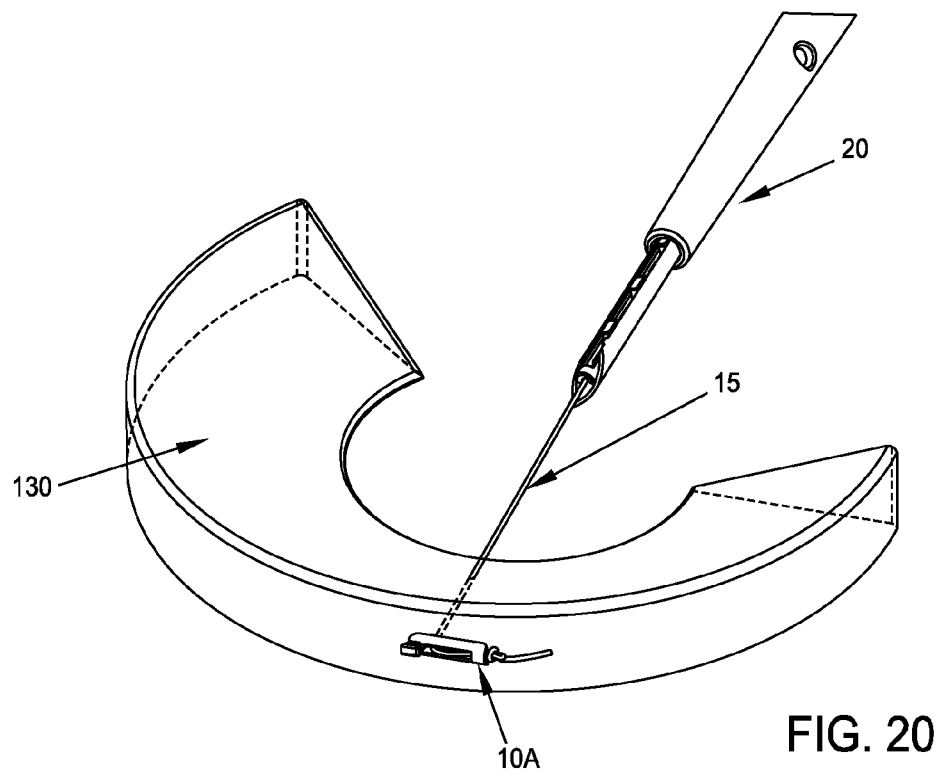
Figure 21:
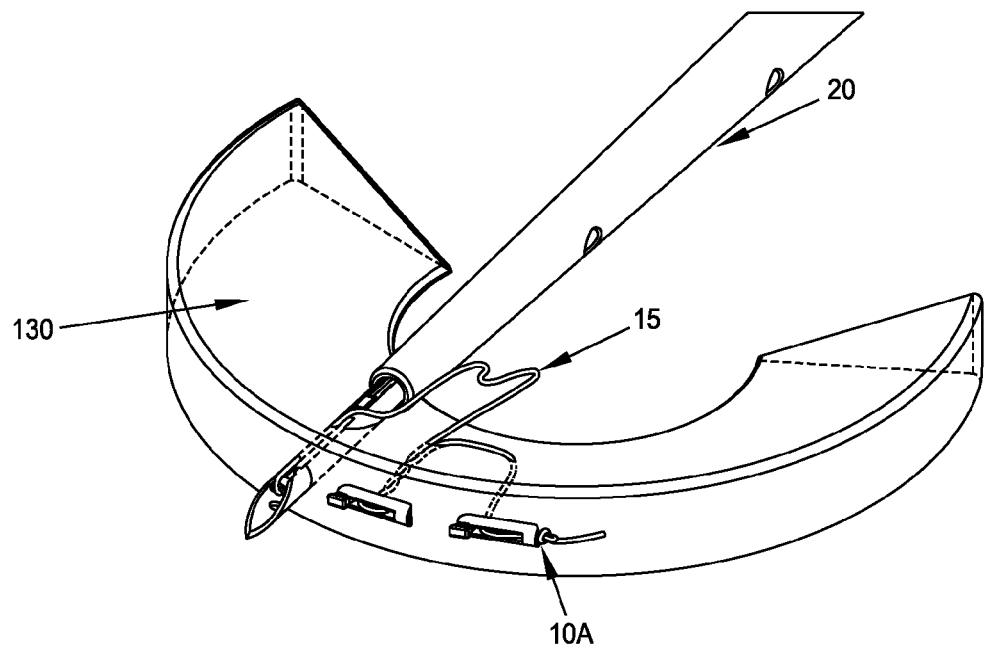
Figure 22:
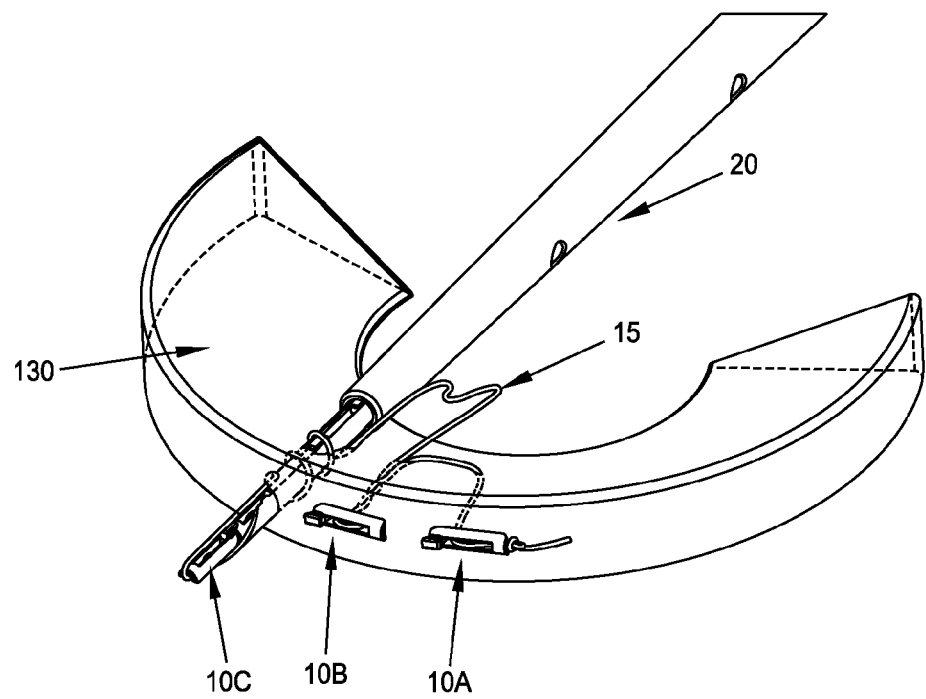

Then, with the suture loose within inserter 20, elongated shaft 85 is withdrawn back out of meniscus 130, with suture 15 paying out of suture spool 120 as this occurs. Then thumb lock 122 is activated so as to bind suture 15 to inserter 20. With suture 15 so bound, inserter 20 is used to tension suture 15 (FIG. 20). As this occurs, cleat 10 is turned, with suture 15 slipping into wide section 60 of proximal slot 55 and then into narrow section 65 of proximal slot 55. Thus, at this point suture 15 will extend through recess 75 and narrow section 65 of proximal slot 55 of the deployed cleat 10. Then thumb lock 122 is released so as to once again free suture 15 from inserter 20.

Thereafter, further cleats may be set as will hereinafter be discussed. For purposes of illustration but not limitation, the setting of such subsequent cleats will hereinafter be discussed in the context of FIGS. 21-25, and specifically in the context of setting cleat 10C after cleat 10B has already been set.

Figure 23:
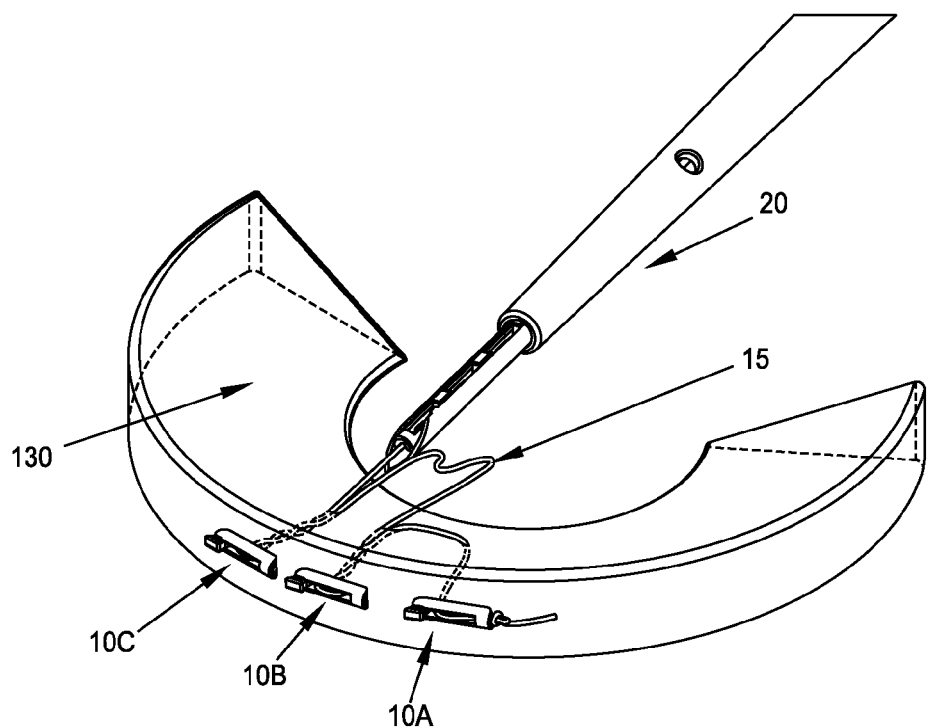
Figure 24:
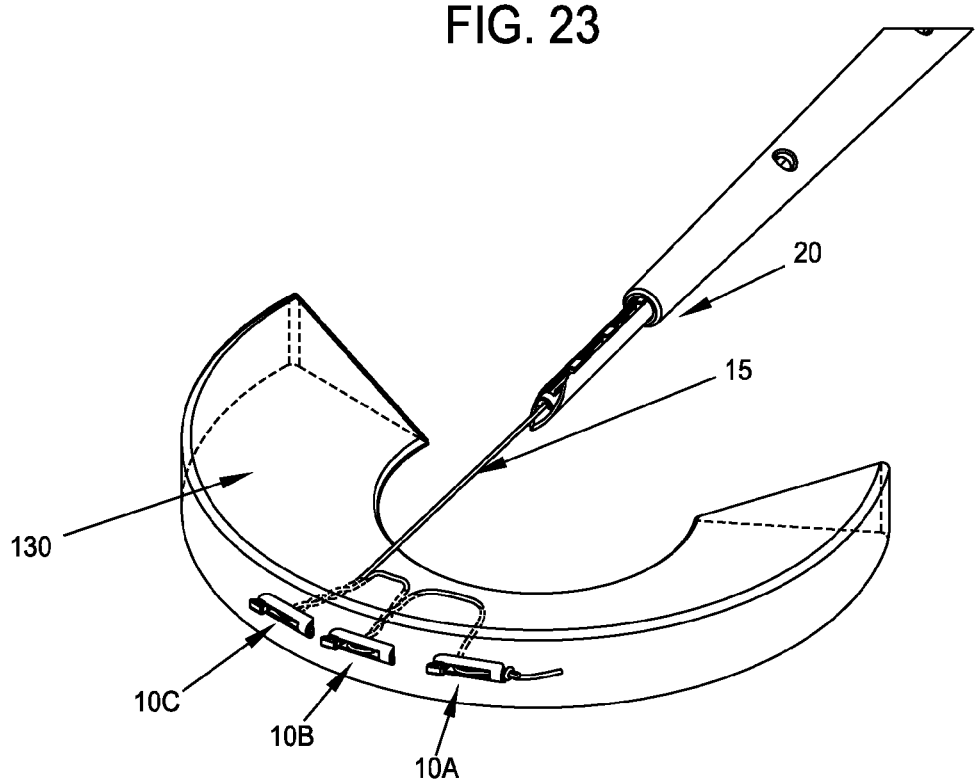
Figure 25:
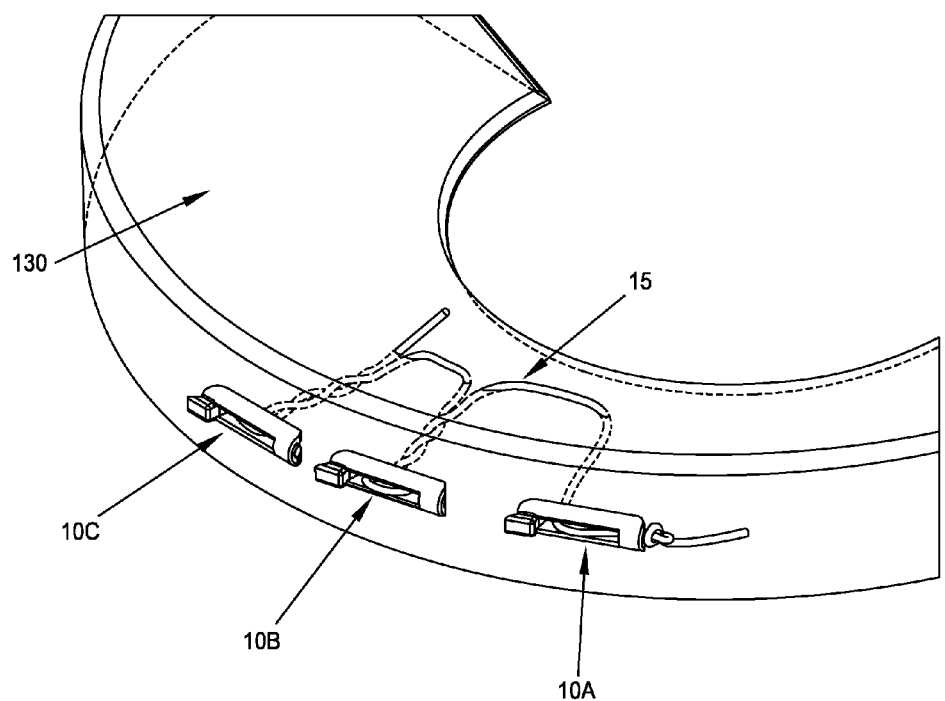
Figure 26:
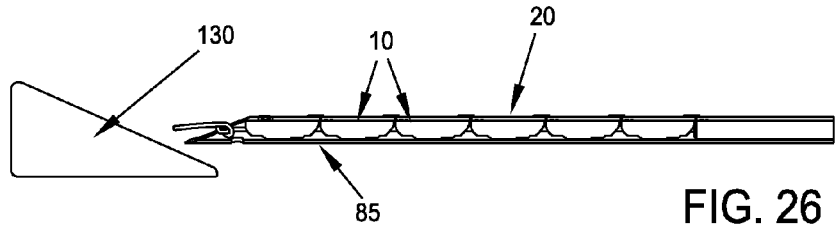
Figure 27:
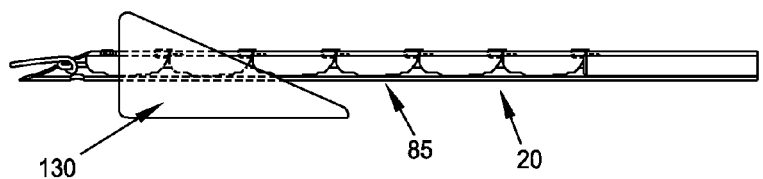
Figure 28:
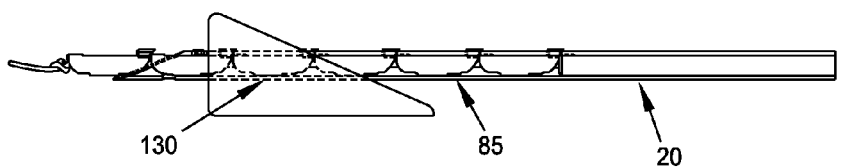
Figure 29:
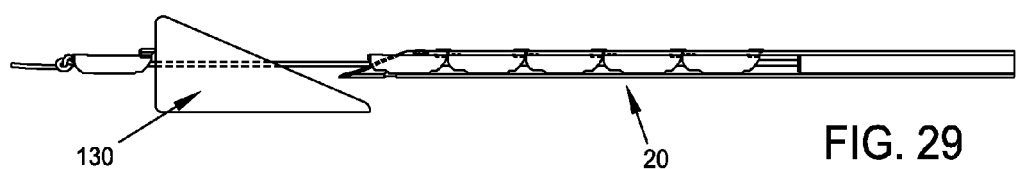

With suture 15 not under tension, inserter 20 is moved to another location (e.g., laterally in FIG. 21, although it could also be moved vertically, or some combination of laterally and vertically) by an appropriate distance, re-inserted across tear 125, passed out the far side of meniscus 130 (FIG. 21), rotated several times about its axis (FIG. 22), and then another cleat 10 (e.g., cleat 10C in FIG. 22) is ejected from elongated shaft 85. As cleat 10C is ejected from elongated shaft 85, it follows the suture path leading back to cleat 10B, turning on the far side of the meniscus (FIG. 23). Then, with suture 15 still not under tension, inserter 20 is withdrawn back across the meniscus, with suture 15 paying out of suture spool 120 as this occurs, and with cleat 10C sliding into proximity with the far side of the meniscus (FIG. 23). Then thumb lock 122 is used to secure suture 15 to inserter 20. With suture 15 secured to inserter 20, inserter 20 is used to tension suture 15 (FIG. 24), i.e., by pulling proximally on inserter 20. As suture 15 is tensioned, the suture loop that extends between cleat 10B and cleat 10C draws down, and further tensioning of suture 15 causes one portion of suture 15 to slip into wide section 60 of proximal slot 55 and then into narrow section 65 of proximal slot 55, and with another portion of the suture slipping into wide section 45 of distal slot 40 and then being forced into the narrow section 50 of distal slot 40 of cleat 10C, whereby to secure suture 15 to cleat 10C in a cleating action (FIG. 25). Thus, at this point, suture 15 will extend through narrow section 50 of distal slot 40, recess 75 and narrow section 65 of proximal slot 55, with the suture being secured to the cleat by virtue of the tight binding fit established between narrow section 50 of distal slot 40 and suture 15. Furthermore, because the suture was rotated on itself one or more times prior to tensioning, the rotated suture on the proximal side of cleat 10C further strengthens the binding of the suture to the cleat.

Significantly, the suture tension established between two adjacent cleats is independent of the suture tension established between others of the cleats. This can be advantageous for a number of reasons, e.g., it permits different tensions to be applied to different portions of the tissue, loss of tension between any two cleats does not undermine tension between others of the cleats, etc.

Thus, the suture length extending between the first-deployed cleat (i.e., cleat 10A in FIG. 25) and the second-deployed cleat (i.e., cleat 10B in FIG. 25) is maintained under tension so as to hold tear 125 closed.

This operation may thereafter be repeated as many times as is necessary in order to close the tear. See, for example, FIG. 25, where three cleats 10, all connected by a single suture 15, are used to close a tear in the meniscus using a complex running stitch. This ability to set a variable number of cleats in the repair procedure, limited only by the number of cleats held in inserter 20, is a significant advance in the art.

In one preferred form of the invention, the first cleat 10 in inserter 20 may have suture 15 permanently secured thereto, e.g., prior to insertion of the inserter into the meniscus. By way of example but not limitation, suture 15 may be glued, welded or otherwise secured to first cleat 10. Furthermore, where suture 15 is so secured to first cleat 10, the terminated suture may terminate substantially within the cleat or it may extend out of the cleat, as desired.

Significantly, since suture 15 is secured to each deployed cleat, the failure of any one suture stitch does not threaten the integrity of the remainder of the repair. Indeed, if a suture stitch were to fail (e.g., break), it would not disrupt the intact stitches in the remainder of the repair. The removed cleat could then be replaced by two or more additional cleats so as to reinforce the repair.

It will be appreciated that the holding power of each cleat 10 on suture 15 is a function of the cleating action provided by that cleat on suture 15. It will also be appreciated that this cleating action is largely a function of the binding interference fit which is established between the suture and narrow section 50 of distal slot 40, since the suture makes a loose fit through recess 75 and a sliding fit with narrow section 65 of proximal slot 55.

Figure 30:
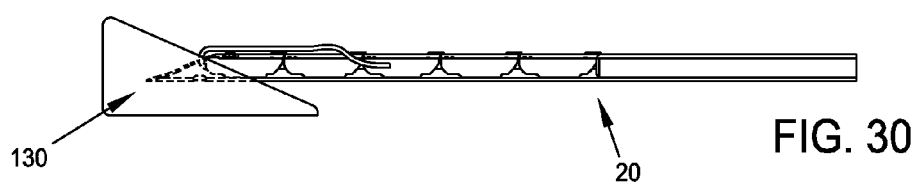
Figure 31:
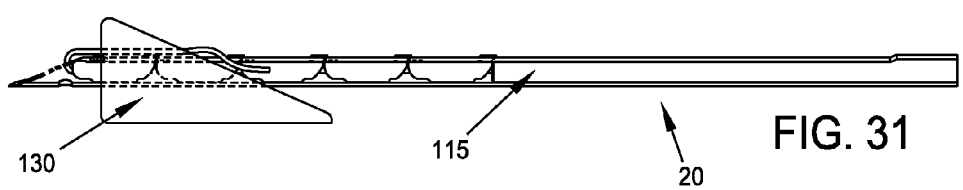

FIGS. 26-29 are schematic views showing, in side view, the first cleat 10 in an inserter 20 being deployed on the far side of meniscus 130. FIGS. 30 and 31 are schematic views showing, in side view, a subsequent cleat 10 being deployed on the far side of meniscus 130. Among other things, FIGS. 26-29 show how the lead cleat in inserter 20 always remains fully within lumen 90 of elongated shaft 85 during meniscus penetration. FIGS. 30 and 31 show how a subsequent cleat may engage tissue during meniscus penetration, however, the cleat slips back into lumen 90 of elongated shaft 85 upon engagement with opposing tissue so that it is the elongated shaft, and not the cleats, which resist the forces imparted by the tissue during meniscus penetration.

In the foregoing description, the cleating action of cleat 10 on suture 15 is provided by narrow section 50 of distal slot 40, and proximal slot 55 is sized so as to slidably receive suture 15. However, if desired, proximal slot 55 (e.g., narrow section 65) may be sized so as to also provide a cleating action on suture 15.

Thus, the present invention provides a meniscal repair system which comprises a plurality of cleats having a single suture strand extending therethrough, wherein each of the cleats can be singly deployed within the body, with each single cleat acting as an independent fixation point for the suture strand. The ability to independently lock the suture to each cleat (such as with the cleating feature provided for each cleat) provides the ability for each cleat to act as an independent fixation point for the suture strand. Furthermore, these independent fixation points allow the suture, running from one cleat to the next cleat, to act as an independent suture stitch. Additionally, the entire contiguous repair construct consists of multiple independent suture stitches extending between multiple adjacent cleats, with the construct such that if one or more stitches are damaged or become loose or disengaged from a cleat, the other suture stitches are unaffected. Also, the ability to individually tighten each suture stitch (i.e., the suture strand extending between adjacent cleats) by drawing the suture through the deployed cleat's locking feature permits the desired suture tension to be achieved.

The present invention provides the ability to position variable suture patterns across the torn meniscus in a contiguous fashion. Significantly, the repairing construct can have more than two points of fixation to the meniscus using a single strand of suture, and does not require any suture tying.

Also, the present invention provides the ability to remove a cleat from a deployed suture construct without disrupting previously-deployed cleats. This would be accomplished by sliding the dislodged implant along the suture strand outside of the body and breaking or cutting the implant without damaging the suture. The user can then continue to deliver subsequent implants from the same device to complete the repair.

And the present invention provides the ability to cut the suture strand after two or more implants have been deployed into the body, and then secure the deployed suture strand to the leading cleat in the inserter (e.g., by knotting) so that the user can continue to deploy subsequent unused cleats still residing within the inserter as part of the repair construct.

The present invention provides a gating mechanism for singly deploying each cleat from the inserter, e.g., fin 80, slot 105 and projection 106.

Furthermore, the present invention provides an approach for wrapping or twisting the suture around the inserter prior to ejection of a cleat so as to form a suture loop around the suture emanating from the cleat, so that subsequent tightening of the suture through the cleat draws the wrapped suture loop towards the cleat and further secures the suture to the cleat.

MODIFICATIONS

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. A method for securing a first object to a second object, the method comprising the steps of:
   providing a system comprising:
      a suture;
      at least two cleats, each cleat comprising:
         an elongated cylindrical body having a distal end, a proximal end, a longitudinal axis extending between the distal end and the proximal end, a cylindrical outer surface radially offset from the longitudinal axis, a first side having a distal slot opening on the cylindrical outer surface of the body and extending from the distal end of the body proximally along the longitudinal axis of the body, and a proximal slot opening on the cylindrical outer surface of the body and extending from the proximal end of the body distally along the longitudinal axis of the body, and a second side having a recess extending from a point removed from the distal end of the body to a point removed from the proximal end of the body, the recess being in communication with the distal slot and the proximal slot;

the distal slot comprising a wide section extending from the distal end of the body and a narrow section extending from the wide section toward the proximal end of the body and terminating in the body, wherein the wide section has a width such that the suture is slidably accommodated therein and the narrow section has a width such that the suture is bound therein;

wherein the suture is initially disposed within the body so that the suture extends from the proximal slot through the recess and out the wide section of the distal slot of each of the at least two cleats so that the suture is slidable relative to the at least two cleats; and an inserter, the inserter comprising a hollow elongated shaft having a sharp point disposed eccentric to the longitudinal axis of the hollow elongated shaft, and further wherein the suture and the at least two cleats are disposed within the lumen of the hollow elongated shaft;

passing the inserter through the first object and the second object so that the sharp point of the inserter resides on the far side of the second object;

ejecting the first cleat on the far side of the second object;

withdrawing the inserter out of the first object and the second object;

tensioning the suture so that the suture is drawn into the narrow section of the distal slot of the first cleat, whereby to bind the suture to the first cleat;

moving the inserter to another location on the first object;

passing the inserter back through the first object and the second object so that the sharp point of the inserter resides on the far side of the second object;

ejecting the second cleat on the far side of the second object;

withdrawing the inserter out of the first object and the second object; and tensioning the suture so that the suture is drawn into the narrow section of the distal slot of the second cleat, whereby to bind the suture to the second cleat.

2. A method according to claim 1 wherein the system comprises a third cleat, and further wherein the method comprises the additional steps of:

moving the inserter to another location on the first object;

passing the inserter back through the first object and the second object so that the sharp point of the inserter resides on the far side of the second object;

ejecting the third cleat on the far side of the second object;

withdrawing the inserter out of the first object and the second object; and tensioning the suture so that the suture is drawn into the narrow section of the distal slot of the third cleat, whereby to bind the suture to the third cleat.

3. A method according to claim 2 wherein the suture is drawn into the narrow section of the distal slot of the third cleat after the inserter is withdrawn from the first and second objects.

4. A method according to claim 1 wherein the suture is not held under tension when the first and second cleats are ejected on the far side of the second object.

5. A method according to claim 1 wherein the inserter is rotated while disposed in the first object and the second object so as to wrap the suture onto itself.

6. A method according to claim 1 wherein the proximal slot of each cleat comprises a wide section extending from the proximal end of the body and a narrow section extending from the wide section toward the distal end of the body and terminating in the body, wherein the wide section has a width such that the suture is slidably accommodated therein and the narrow section has a width such that the suture is bound therein.

7. A method according to claim 1 wherein the first object comprises a first portion of the meniscus and the second object comprises a second portion of the meniscus.

8. A method for securing a first object to a second object, the method comprising the steps of:

providing a system comprising:
   a suture;
   a leading cleat, the suture being connected to the leading cleat so that the leading cleat can restrict retrograde movement of the suture relative to the leading cleat;
   a trailing cleat, the trailing cleat comprising:
      an elongated cylindrical body having a distal end, a proximal end, a longitudinal axis extending between the distal end and the proximal end, a cylindrical outer surface radially offset from the longitudinal axis, a first side having a distal slot opening on the cylindrical outer surface of the body and extending from the distal end of the body proximally along the longitudinal axis of the body, and a proximal slot opening on the cylindrical outer surface of the body and extending from the proximal end of the body distally along the longitudinal axis of the body, and a second side having a recess extending from a point removed from the distal end of the body to a point removed from the proximal end of the body, the recess being in communication with the distal slot and the proximal slot;
   the distal slot comprising a wide section extending from the distal end of the body and a narrow section extending from the wide section toward the proximal end of the body and terminating in the body, wherein the wide section has a width such that the suture is slidably accommodated therein and the narrow section has a width such that the suture is bound therein;
   wherein the suture is initially disposed within the body so that the suture extends from the proximal slot through the recess and out the wide section of the distal slot of the trailing cleat so that the suture is slidable relative to the trailing cleat; and
   an inserter, the inserter comprising a hollow elongated shaft having a sharp point, and further wherein the suture, the leading cleat and the trailing cleat are disposed within the lumen of the hollow elongated shaft;

passing the inserter through the first object and the second object so that the sharp point of the inserter resides on the far side of the second object;

ejecting the leading cleat on the far side of the second object;

withdrawing the inserter out of the first object and the second object;

moving the inserter to another location on the first object;

passing the inserter back through the first object and the second object so that the sharp point of the inserter resides on the far side of the second object;

ejecting the trailing cleat on the far side of the second object;

withdrawing the inserter out of the first object and the second object; and tensioning the suture so that the suture is drawn into the narrow section of the distal slot of the trailing cleat, whereby to bind the suture to the trailing cleat.

9. A method according to claim 8 wherein the system comprises a second trailing cleat, and further wherein the method comprises the additional steps of:
moving the inserter to another location on the first object;
passing the inserter back through the first object and the second object so that the sharp point of the inserter resides on the far side of the second object;
ejecting the second trailing cleat on the far side of the second object;
withdrawing the inserter out of the first object and the second object; and
tensioning the suture so that the suture is drawn into the narrow section of the distal slot of the second trailing cleat, whereby to bind the suture to the second trailing cleat.

10. A method according to claim 9 wherein binding the suture to the second trailing cleat is not dependent upon binding the suture to the first trailing cleat.

11. A method for securing a first object to a second object, the method comprising:
providing a suture and a plurality of cleats slidably mounted on the suture, wherein each of the plurality of cleats comprises:
an elongated cylindrical body having a distal end, a proximal end, a longitudinal axis extending between the distal end and the proximal end, a cylindrical outer surface radially offset from the longitudinal axis, a first side having a distal slot opening on the cylindrical outer surface of the body and extending from the distal end of the body proximally along the longitudinal axis of the body, and a proximal slot opening on the cylindrical outer surface of the body and extending from the proximal end of the body distally along the longitudinal axis of the body, and a second side having a recess extending from a point removed from the distal end of the body to a point removed from the proximal end of the body, the recess being in communication with the distal slot and the proximal slot;
the distal slot comprising a wide section extending from the distal end of the body and a narrow section extending from the wide section toward the proximal end of the body and terminating in the body, wherein the wide section has a width such that the suture is slidably accommodated therein and the narrow section has a width such that the suture is bound therein;
wherein the suture is initially disposed within the body so that the suture extends from the proximal slot through the recess and out the wide section of the distal slot of each of the plurality of cleats so that the suture is slidable relative to the plurality of cleats;
passing one end of the suture and a first cleat through the first object and the second object;
tensioning the suture so as to secure the suture to the first cleat;
passing a subsequent portion of the suture and a second cleat through the first object and the second object; and
tensioning the suture so as to secure the suture to the second cleat.

12. A method for securing a first object to a second object, the method comprising:
providing a suture, a leading cleat connected to the suture, and a plurality of trailing cleats slidably mounted on the suture, wherein each of the plurality of trailing cleats comprises:
an elongated cylindrical body having a distal end, a proximal end, a longitudinal axis extending between the distal end and the proximal end, a cylindrical outer surface radially offset from the longitudinal axis, a first side having a distal slot opening on the cylindrical outer surface of the body and extending from the distal end of the body proximally along the longitudinal axis of the body, and a proximal slot opening on the cylindrical outer surface of the body and extending from the proximal end of the body distally along the longitudinal axis of the body, and a second side having a recess extending from a point removed from the distal end of the body to a point removed from the proximal end of the body, the recess being in communication with the distal slot and the proximal slot;
the distal slot comprising a wide section extending from the distal end of the body and a narrow section extending from the wide section toward the proximal end of the body and terminating in the body, wherein the wide section has a width such that the suture is slidably accommodated therein and the narrow section has a width such that the suture is bound therein;
wherein the suture is initially disposed within the body so that the suture extends from the proximal slot through the recess and out the wide section of the distal slot of each of the plurality of trailing cleats so that the suture is slidable relative to the plurality of trailing cleats;
passing one end of the suture and the leading cleat through the first object and the second object at a first location;
passing a subsequent portion of the suture and a first trailing cleat through the first object and the second object at a second location, the second location being displaced from the first location;
tensioning the suture so as to secure the suture to the first trailing cleat, whereby to create a first stable fastening construct by means of the leading cleat, the first trailing cleat and the suture tensioned therebetween;
passing another subsequent portion of the suture and a second trailing cleat through the first object and the second object at a third location, the third location being displaced from the second location; and
tensioning the suture so as to secure the suture to the second trailing cleat, whereby to create a second stable fastening construct by means of the first trailing cleat, the second trailing cleat and the suture tensioned between.

13. A method according to claim 12 wherein the stability of the first stable fastening construct is not dependent upon the stability of the second stable fastening construct.

* * * * *